United States Patent [19]

Pohndorf

[11] Patent Number: 4,967,755
[45] Date of Patent: Nov. 6, 1990

[54] ELECTROMEDICAL LEAD WITH PRESSURE SENSOR

[75] Inventor: Peter J. Pohndorf, Stillwater, Minn.

[73] Assignee: Medtronic, Inc., Minneapolis, Minn.

[21] Appl. No.: 316,702

[22] Filed: Feb. 28, 1989

[51] Int. Cl.$^5$ .......................... A61B 5/215; A61N 1/05
[52] U.S. Cl. ....................................... 128/675; 128/786
[58] Field of Search ..................... 128/784, 786, 419 P, 128/673, 675, 642, 785

[56] References Cited

U.S. PATENT DOCUMENTS

| | | | |
|---|---|---|---|
| 4,485,813 | 12/1984 | Anderson et al. | 128/675 |
| 4,600,017 | 7/1986 | Schroeppel | 128/784 |
| 4,770,177 | 9/1988 | Schroeppel | 128/786 |
| 4,791,935 | 12/1988 | Baudino et al. | 128/637 |
| 4,815,469 | 3/1989 | Cohen et al. | 128/634 |

FOREIGN PATENT DOCUMENTS 0178528  4/1986  European Pat. Off. .
WO87/01947 4/1987 PCT Int'l Appl. .

Primary Examiner—Lee S. Cohen
Attorney, Agent, or Firm—Reed A. Duthler

[57] ABSTRACT

A body implantable lead including a stimulation electrode located at its distal end, a ring electrode located proximal to its distal end, and a pressure sensor. The lead is adapted to be used in conjunction with a stylet, which passes through the body of the lead from its proximal end to its distal end. The pressure sensor is integrated mechanically with the ring electrode, and is provided with a stylet tube which provides electrical connection to the tip electrode and allows passage of the stylet to the distal end of the lead. The pressure sensor includes a generally planar diaphragm, located within the ring electrode, communicating with the exterior of the ring electrode by means of one or more apertures. The stylet tube is mounted within the ring electrode adjacent to but insulated from the pressure sensor diaphragm.

8 Claims, 5 Drawing Sheets

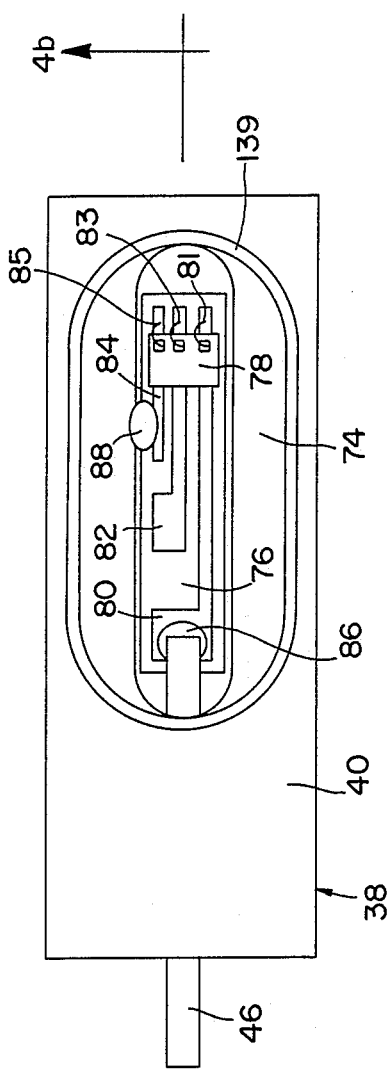
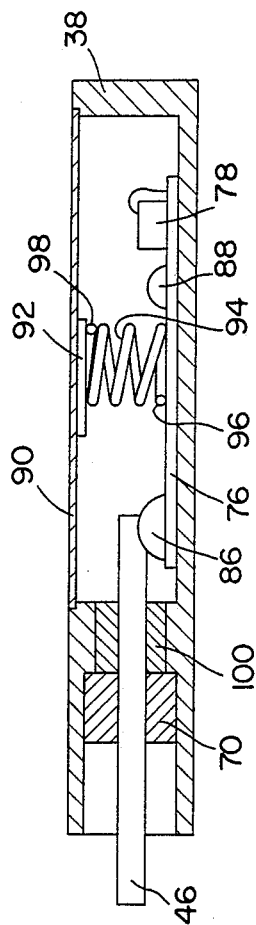
FIG. 4a
FIG. 4b

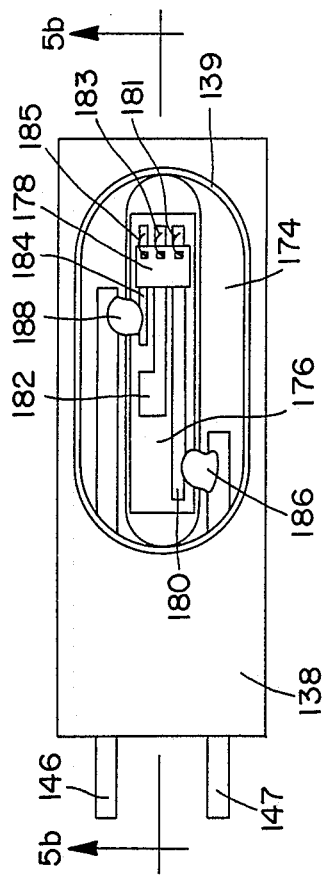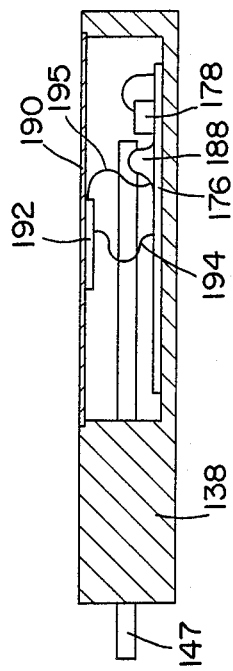
FIG.5a
FIG.5b

ELECTROMEDICAL LEAD WITH PRESSURE SENSOR

BACKGROUND OF THE INVENTION

This invention relates generally to medical electrical leads, and in more particular to cardiac pacing leads of the type combining pacing and pressure sensing functions on a single lead.

U.S. Pat. No. 4,407,296 issued to Anderson discloses an implantable pressure sensing lead in which the pressure transducer is mounted at the distal end of the lead, with the diaphragm oriented perpendicular to the axis of the lead. The diaphragm is protected by means of a slotted grill, which is intended to lie adjacent the tissue of the heart when the lead is implanted.

U.S. Pat. No. 4,485,813 issued to Anderson et al also discloses the incorporation of a pressure transducer into a cardiac pacing lead. In all illustrated embodiments, the transducer is generally cylindrical in configuration, carrying a pressure sensing diaphragm at its distal end, oriented perpendicularly to the axis of the lead. In some embodiments, the pressure sensor is located at the distal end of the lead. In these embodiments, an electrode having an aperture is located over the pressure transducer. In use, the electrode is intended to contact heart tissue. In other embodiments, the pressure transducer is located proximal to the distal end of the lead and includes a side facing aperture exposed to the surface of the diaphragm, through which pressure may be sensed. In both embodiments, the conductive case of the pressure transducer serves as part of the electrical path to the stimulating electrode located at the tip of the lead.

As discussed in the Anderson et al patent, location of the pressure transducer at the distal end of the lead is appropriate if the motion of the ventricular wall is the signal of particular interest. Location of the pressure transducer proximal to the distal end of the lead is desirable where blood pressure is the primary signal of interest.

SUMMARY OF THE INVENTION

In the leads disclosed in the above-cited Anderson et al patent, the sensor body was used as a conductor, coupling the pacemaker to the tip electrode. This precluded use of the pressure sensor housing as an indifferent electrode, to be used in conjunction with the tip electrode, and required that the housing be provided with an insulative covering. Because the pressure sensing diaphragm was perpendicular to the axis of the lead, the structure of the sensor housings precluded passage of a stylet through the sensor body. It is desirable in a cardiac pacing lead to be able to use a stylet to locate the distal tip of the lead. It is also desirable to be able to pass the stylet at least to the immediate vicinity of the tip electrode in order to perform that function.

The present invention provides a pressure transducer assembly which permits for passage of the stylet, through the pressure sensor assembly, without compromising hermeticity of the pressure transducer. Furthermore, the pressure transducer assembly of the present invention includes provision for passage of a conductor through the transducer assembly, insulated from the outer surface of the pressure transducer assembly. This allows the outer surface of the transducer assembly to be used as a ring electrode. These objects are accomplished by a sensor assembly in which the sensing diaphragm lies parallel to the axis of the lead, adjacent a lumen defined within the sensor assembly. A conductive metal tube passes through the lumen, insulated from the remainder of the sensor assembly. This conductive metal tube serves both to provide electrical connection to the pacing electrode at the tip of the lead and to allow passage of a stylet to the tip of the lead.

Because the orientation of the sensing diaphragm is parallel to the lead axis, production of a sensor diaphragm having an oblong, rather than a circular configuration is feasible. An oblong sensor diaphragm displaying a desired surface area will fit into a smaller lead body diameter than a corresponding diaphragm having a circular configuration. The pressure sensor assembly of the present invention is configured so that it may be incorporated in a bipolar cardiac pacing lead, in which the sensor assembly has a diameter as small as 8 French, simplifying insertion and passage of the pacing lead.

The pressure sensor of the present invention like the pressure sensors of the prior art is a rigid assembly. Generally, in the vicinity of the distal end of the pacing lead, a certain amount of flexibility is desirable in order to avoid undue pressure being placed on the heart tissue by the pacing lead. By combining the pressure sensor and the ring electrode into a single assembly in the present lead, incorporation of this additional rigid structure within the pacing lead is accomplished without reducing the flexibility of the pacing lead compared to conventional bipolar pacing leads.

BRIEF DESCRIPTION OF THE DRAWINGS

FIG. 4A shows a top plan view of the pressure sensor of the present invention, with its pressure sensing diaphragm removed for the sake of illustration.

FIG. 4B shows a side, cutaway view through the pressure sensor illustrated in FIG. 4A.

FIG. 5A shows a top plan view of an alternative embodiment of a pressure sensor for use in a medical lead for temporary use.

FIG. 5B shows a side, cutaway view through the pressure sensor illustrated in FIG. 5A.

DETAILED DESCRIPTION OF THE INVENTION

Figure 1:
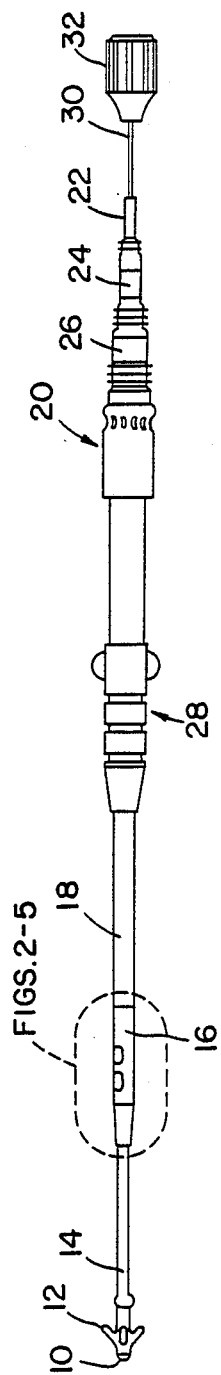
FIG. 1 shows a plan view of a pacing lead according to the present invention.

FIG. 1 is a plan view of a cardiac pacing lead employing the present invention. At the distal end of the lead is located an electrode 10, which functions to stimulate the heart tissue. Electrode 10 is held in engagement with heart tissue by means of flexible tines 12, which engage with the trabeculae in the apex of the ventricle of the heart. Tines 12 are described in more detail in U.S. Pat. No. 3,902,501, issued to Citron et al. A flexible insulative sheath 14 extends from electrode 10 to ring electrode 16. Pacing pulses are delivered between electrode 10 and ring electrode 16. Electrodes 10 and 16 may also be used to sense the natural electrical activity of the heart. Located within ring electrode 16 is a pressure transducer, which senses the pressure of the blood within the heart. Information regarding the blood pressure within the heart is used to modulate the pacing rate of a cardiac pacemaker, as described in the above-cited Pat. No. 4,485,813, issued to Anderson et al, Dec. 4, 1984, for an "IMPLANTABLE DYNAMIC PRESSURE TRANSDUCER SYSTEM", incorporated by reference herein in its entirety.

Extending proximally from ring electrode 16 is a second insulative sheath 18, which extends to the connector assembly 20, located at the proximal end of the lead. Connector assembly 20 is described in more detail in commonly assigned, copending patent application Ser. No. 07/198,540, by Doan et al, for a "CONNECTOR FOR MULTICONDUCTOR PACING LEADS", filed May 25, 1988, also incorporated herein by reference in its entirety. Connector assembly 20 is provided with three cylindrical conductive surfaces 22, 24 and 26. Connector surface 22 is coupled to tip electrode 10. Connector surfaces 26 and 24 are coupled to ring electrode 16 and to the circuitry within the pressure sensor, respectively. Surrounding insulative sheath 18 is an anchoring sleeve 28, which is used to secure the lead at its point of venous insertion. The basic operation of an anchoring sleeve is described in U.S. Pat. No. 4,437,475, issued to White. Shown emerging from the proximal end of the lead is a stylet 30, which has located on its proximal end a knob 32. Stylet 30 extends through the lead body, terminating in the vicinity of electrode 10. An appropriate form of stylet is disclosed in U.S. Pat. No. 4,498,482, issued to Williams for a "TRANSVENOUS PACING LEAD HAVING IMPROVED STYLET", incorporated herein by reference in its entirety.

During pacing of the heart, an electrical impulse is delivered between electrodes 10 and 16 via connector surfaces 22 and 26. During sensing of electrical activity within the heart, the electrical potential difference between electrodes 10 and 16 is provided to the pacemaker via connector surfaces 26 and 22. During operation of the pressure transducer located within ring electrode 16, an electrical current is applied to connector surfaces 24 and 26. The current drawn by the pressure transducer will vary depending upon the ambient blood pressure surrounding ring electrode 16. The current level is used by the pacemaker to determine blood pressure within the ventricle at the time of sensor activation.

Figure 2:
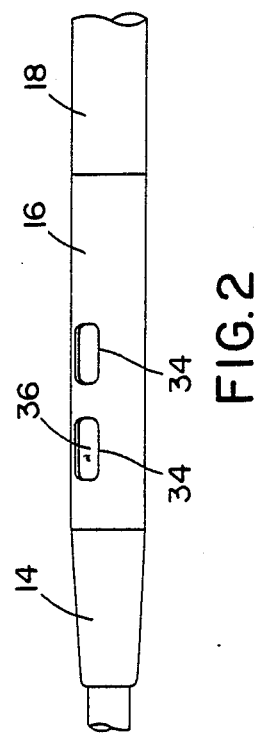
FIG. 2 shows a top plan view of the lead of FIG. 1, in the vicinity of the ring electrode.

FIG. 2 shows a top plan view of the lead of FIG. 1, in the vicinity of ring electrode 16. In this view, it can be seen that ring electrode 16 is provided with four windows or apertures 34. Ring electrode 16 takes the form of a hollow conductive metal cylinder, and apertures 34 extend through the exterior of ring electrode 16 and into its interior lumen. Located within the interior lumen of ring electrode 16, in the vicinity of apertures 34, is a molded plastic member 36, which transmits the blood pressure external to the lead to the pressure transducer located within ring electrode 16.

Figure 3A:
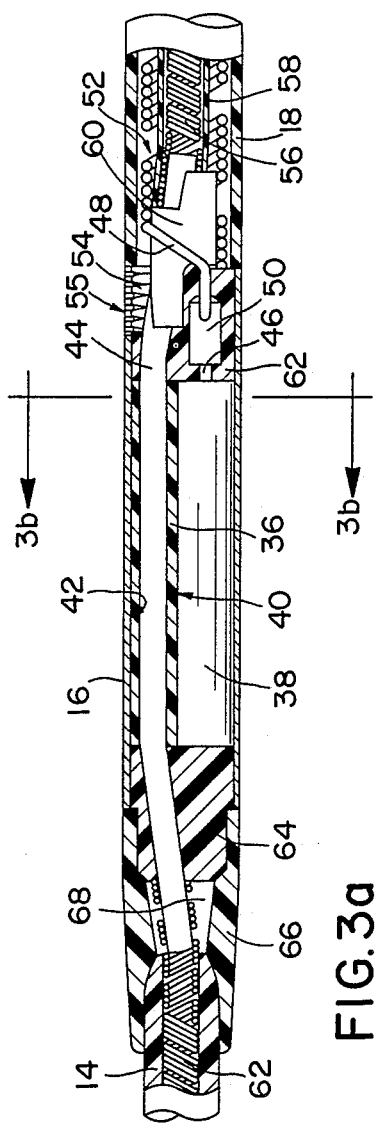
FIG. 3A shows a side, cutaway view of the lead of FIG. 1, in the vicinity of the ring electrode/pressure sensor assembly.

FIG. 3A is a side, cutaway view showing the mechanical interrelation of components in the vicinity of ring electrode 16. Located within ring electrode 16 is a sensor body 38, which generally takes the form of one-half of a cylinder. Sensor body 38 is fabricated of a conductive biocompatible metal, and is in electrical and mechanical contact with ring electrode 16. The interior surface 42 of ring electrode 16 and the upper surface 40 of sensor 38 define a lumen with a semicircular cross section, through which a tubular stylet guide 44 passes.

Stylet guide 44 is located within the lumen by means of the resilient plastic member 36. The upper surface 40 of sensor body 38 is the mounting location for a pressure sensing diaphragm. Pressure exterior to the lead is transmitted to the diaphragm through apertures 34 (FIG. 2) by means of resilient plastic member 36.

Located within sensor body 38 is the circuitry which comprises the pressure transducer. This circuitry is coupled to the exterior of sensor body 38 by means of a feedthrough pin 46. Wire 46 is coupled to a coiled insulated conductor 48 by means of ferrule 50. Conductor 48 is one coil of a multipolar coil 52. The remainder of the individual insulated wires 54 of multipolar coil 52 are coupled to ring electrode 26 by means of laser welding or other appropriate method. Their ends are stripped of insulation and welded into a slot 55. Any spaces between wires 54 are backfilled with silicone rubber or other appropriate material.

At its proximal end, stylet tube 44 is coupled to a multifilar coiled conductor 56, which extends proximally to the connector assembly 20, illustrated in FIG. 1, where it is coupled to connector surface 22. Surrounding multifilar coil 56 is an insulative sheath 58, which insulates multifilar coil 56 from contact with multipolar coil 52. The conductors of multipolar coil 52, multifilar coil 56, stylet tube 44 and insulative sheath 58 are retained in their respective positions relative to one another by means of a plastic spacer 60. The area between the proximal end of sensor body 38 and spacer 60 is backfilled with medical adhesive to further stabilize the structure.

The distal end of stylet tube 44 is coupled to a second multifilar coil 62 which extends distally from stylet tube 44 to the distal end of the lead, where it is coupled to tip electrode 10 (FIG. 1). A second plastic spacer 64, in conjunction with a tapered insulative sheath segment 66, maintains the orientation of stylet tube 44 as it emerges from the distal end of ring electrode 16. The area 68 surrounding the distal end of stylet tube 44 may also be advantageously backfilled with adhesive, if desired, to further stabilize the assembly.

Figure 3B:
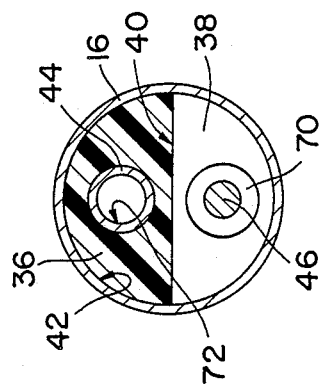
FIG. 3B shows a cross sectional view through the ring electrode/pressure sensor assembly.

FIG. 3B shows a cross section through the portion of the lead illustrated in FIG. 3A. Wire 46 emerges from sensor body 38 through a feedthrough 70. Plastic member 36 fills the semicircular lumen defined by the interior surface 42 of ring electrode 16 and the upper surface 40 of sensor body 38. Sensor tube 44 is seen to be provided with a lumen 72, through which a stylet may pass.

Ring electrode 16, sensor body 38, and stylet tube 44 are all preferably made of conductive, biocompatible metals such as titanium, stainless steel, MP35N alloy, or platinum. Feedthrough 70 is preferably a sapphire or glass feedthrough. Resilient plastic member 36, sheaths 14, 18 and 66 (FIG. 3A) are preferably fabricated of a biocompatible plastic such as silicone rubber or polyurethane. Plastic spacers 60 and 64 are preferably fabricated of relatively rigid biocompatible plastics such as epoxy or Delrin ®.

FIG. 4A shows a plan view of the top of sensor body 38, as seen from above. In this view, it can be seen that sensor body 38 is provided with an internal chamber 74 in which a hybrid circuit 78, and three conductive paths 80, 82 and 84, deposited upon the hybrid substrate 76 using conventional thick film printed circuit technology. Wire 46 is coupled to conductive path 80 by means of conductive epoxy 86. Conductive path 84 is coupled to the interior surface of sensor body 38 by means of conductive epoxy 88. Conductive path 82 serves as a connection point for a field effect transistor, attached to the diaphragm of the pressure sensor, not visible in this view.

FIG. 4B shows a side, cutaway view of the sensor body illustrated in FIG. 4A. In this view, however, the sensor diaphragm 90 has been attached, and is visible in cross section. Diaphragm 90 is preferably fabricated of the same metal, e.g. stainless steel or titanium, as sensor body 38, so that it may be laser welded around its circumference, to provide a structure which is highly resistant to corrosion. In the configuration illustrated, diaphragm 90 is approximately 0.214 inches long, approximately 0.084 inches wide, and approximately 0.003 inches thick. A piezoelectric crystal 92 is coupled to the lower surface of diaphragm 90 and, when diaphragm 90 is flexed, generates an electrical signal. Crystal 92 is electrically coupled to diaphragm 90, by means of conductive adhesive, and is coupled to conductive path 82 by means of a coiled conductor 94, which is mechanically and electrically coupled to pad 82 by conductive adhesive 96 and to piezoelectric crystal 92 by means of conductive adhesive 98.

In this view, it can be seen that the feedthrough surrounding pin 46 consists of an outer feedthrough 70 and an inner feedthrough 100. Outer feedthrough element 70 is preferably fabricated of glass. Inner feedthrough element 100 is preferably fabricated of ceramic. Pin 46 is preferably fabricated of tantalum. Pin 46, pressure sensor body 38 and feedthrough element 70 and 100 are preferably attached to one another by means of a compression seal.

FIG. 5A illustrates an alternative version of the sensor illustrated in FIGS. 4A and 4B. In this embodiment, the sensor is adapted for use in a temporary pacing lead, and the sensor body is fabricated using plastic. The configuration of the sensor body 138 remains as discussed above in conjunction with FIGS. 4A and 4B. However, two wires 146 and 147 pass through the sensor body 138. Rather than being provided with separate feedthroughs, these wires are simply molded into sensor body 138 during manufacture. The interior cavity 174 of sensor body 138 contains a hybrid circuit 176 which, like the hybrid illustrated above, includes a field effect transistor 178 and three conductive paths 180, 182 and 184. Wire 146 is electrically and mechanically coupled to conductive path 184 by means of conductive epoxy 188. Wire 147 is electrically and mechanically coupled to conductive path 180 by means of conductive epoxy 186. FET 178 is electrically coupled to conductive paths 180, 182 and 184, respectively, by means of wire bonds 181, 183 and 185.

FIG. 5B is a side cutaway view of the pressure sensor illustrated in FIG. 5A, above. In this view, the pressure sensing diaphragm 190 has been added, and is visible in cross section. Pressure sensing diaphragm 190 is preferably fabricated of a biocompatible plastic, as is sensor body 138. Diaphragm 190 may be sonically welded or solvent welded to sensor body 138. Piezoelectric crystal 192 is coupled to conductive paths 182 and 184 by means of wires 194 and 195, respectively. Wires 194 and 195 are coupled to the metallized layers on either side of piezoelectric crystal 192. In order to facilitate connection, it may be desirable to provide a metallized coating on the lower side of diaphragm 192, allowing wire 195 to be bonded to diaphragm 190, rather than directly to the upper surface of crystal 192.

Figure 6:
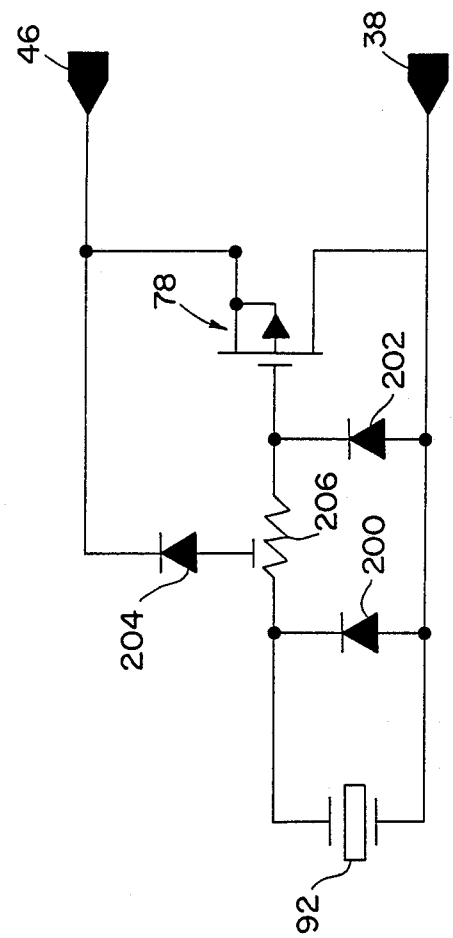
FIG. 6 is a schematic of the pressure sensor illustrated in FIGS. 4A–5B.

The pressure sensors illustrated in FIGS. 4A, 4B, 5A and 5B operate in a similar fashion. The functional schematic of both sensors is illustrated in FIG. 6. For simplicity, operation of the sensor is discussed in conjunction with the sensor illustrated in FIGS. 4A and 4B. Power is applied to the sensor via feedthrough pin 46 and the sensor body 38. During deflection of the diaphragm 90 (FIG. 4B), crystal 92 generates an electrical output which is fed to the gate of field effect transistor 78. The source of field effect transistor 78 is coupled to the feedthrough pin, and the drain to the case. The electrical signal generated by crystal 92 regulates current flow through field effect transistor 78, dependent upon the deflection of the diaphragm. This provides a signal between the feedthrough pin 46 and case 38 which varies with the blood pressure in the heart. Diodes 200, 202, 204 and resistor 206 are formed integral with the substrate of field effect transistor 78 and serve to limit voltages applied to the transistor.

Although the invention as illustrated and described takes the form of a bipolar pacing lead in which the pressure sensor assembly also serves as a ring electrode, certain aspects of the invention are believed to be valuable in and of themselves, and may be applicable to other forms of medical electrical leads. As such, the disclosure above should be considered as illustrative, rather than limiting as to the scope of the following claims.

In conjunction with the above specification, I claim:

1. A medical electrical lead, comprising:
    a conductive sensor body, having an exterior surface exposed to the exterior of said lead, said sensor body having a proximal end and a distal end and having a lumen extending from said proximal end to said distal end, said sensor body including a chamber, isolated from said lumen;
    an elongated conductor, extending through said lumen of said sensor body, and extending body proximally and distally from said sensor body, said elongated conductor itself having an internal, longitudinally extending lumen;
    insulator means mounted within said lumen of said sensor body for insulating said elongated conductor from said sensor body;
    sensor means for sensing a physiologic parameter, mounted within said chamber of said sensor body, said sensor body further comprising an aperture through said exterior surface of said sensor body, through which said sensor means senses said physiologic parameter;
    first and second conductor means, for providing electrical communication to said sensor means, extending proximally from said sensor body, one of said conductor means electrically coupled to said sensor body, the other of said conductor means coupled to said sensor means, insulated from said sensor body; and
    an electrode, coupled to said elongated conductor.

2. An electrical lead according to claim 1 wherein said elongated conductor is insulated from said other of said conductor means coupled to said sensor means.

3. A lead according to claim 1 or claim 2 wherein said elongated conductor comprises a metallic tube, extending through said sensor body.

4. A lead according to claim 3 wherein said elongated conductor further comprises first and second coiled conductors, coupled to said metallic tube, said first coiled conductor extending distally from said metal tube, coupled to said electrode, said second coiled conductor extending proximally from said metallic tube.

5. A lead according to claim 1 wherein said sensor means comprises a pressure sensor, and wherein said sensor comprises a diaphragm, operatively exposed to said aperture through said exterior surface of said sensor body.

6. A medical lead according to claim 5 wherein said diaphragm of said pressure sensor is exposed to said lumen through said sensor body, and wherein said aperture through said exterior surface of said sensor body is exposed to said lumen through said sensor body.

7. A lead according to claim 6 wherein said insulator means is resilient, and is exposed to both said diaphragm of said pressure sensor and to said aperture through said exterior surface of said sensor body, whereby pressure external to said sensor body is communicated by means of said insulator means, to the diaphragm of said pressure sensor.

8. A medical lead according to claim 1 wherein said aperture through said exterior surface of said sensor body opens to said lumen through said sensor body.

* * * * *

UNITED STATES PATENT AND TRADEMARK OFFICE
CERTIFICATE OF CORRECTION

PATENT NO. : 4,967,755

DATED : November 6, 1990

INVENTOR(S) : Peter J. Pohndorf

It is certified that error appears in the above-indentified patent and that said Letters Patent is hereby corrected as shown below:

Column 3, Line 67, delete "sensor 38", and insert in its place --sensor body 38--.

Column 6, Line 38, delete "extending body", and insert in its place --extending both--.

Column 7, Line 6, before "sensor", please add --pressure--.

Signed and Sealed this

Fourth Day of October, 1994

Attest:

BRUCE LEHMAN

*Attesting Officer*   *Commissioner of Patents and Trademarks*